United States Patent
Frankel (10) Patent No.: US 10,299,982 B2
(45) Date of Patent: May 28, 2019

(54) SYSTEMS AND METHODS FOR BLIND AND VISUALLY IMPAIRED PERSON ENVIRONMENT NAVIGATION ASSISTANCE

(71) Applicant: David M Frankel, Bethesda, MD (US)

(72) Inventor: David M Frankel, Bethesda, MD (US)

( * ) Notice: Subject to any disclaimer, the term of this patent is extended or adjusted under 35 U.S.C. 154(b) by 69 days.

(21) Appl. No.: 15/657,063

(22) Filed: Jul. 21, 2017

(65) Prior Publication Data

US 2019/0026939 A1     Jan. 24, 2019

(51) Int. Cl.

| | | |
|---|---|---|
| *A61F 9/08* | (2006.01) | |
| *A61H 3/06* | (2006.01) | |
| *G06K 9/00* | (2006.01) | |
| *G06T 5/00* | (2006.01) | |
| *G06T 7/70* | (2017.01) | |
| *G06T 17/05* | (2011.01) | |
| *G06T 19/00* | (2011.01) | |
| *G09B 21/00* | (2006.01) | |

(52) U.S. Cl.
CPC .............. *A61H 3/061* (2013.01); *A61F 9/08* (2013.01); *G06K 9/00671* (2013.01); *G06T 5/006* (2013.01); *G06T 7/70* (2017.01); *G06T 19/00* (2013.01); *G09B 21/001* (2013.01); *G06T 17/05* (2013.01); *G06T 2210/04* (2013.01); *G06T 2210/28* (2013.01)

(58) Field of Classification Search
CPC .... A61H 3/06; A61H 3/061; A61H 2003/063; G02B 27/0189; G02B 2027/0138; A61F 9/08; G06K 9/00671
See application file for complete search history.

(56) References Cited

U.S. PATENT DOCUMENTS

| | | | | |
|---|---|---|---|---|
| 6,055,048 A | * | 4/2000 | Langevin | A61H 3/061 356/237.1 |
| 7,598,976 B2 | * | 10/2009 | Sofer | G09B 21/006 348/62 |
| 8,605,141 B2 | * | 12/2013 | Dialameh | G06F 17/30247 348/157 |
| 8,606,316 B2 | * | 12/2013 | Evanitsky | H04M 1/72594 348/62 |

(Continued)

OTHER PUBLICATIONS

J. Mrovlje, et al, "Distance measuring based on stereoscopic pictures," 9th International PhD Workshop on Systems and Control, Oct. 2008.

(Continued)

*Primary Examiner* — John Villecco (57) ABSTRACT

A method, performed by a mobile device, for assisting blind or visually impaired users navigate a room or a new and unfamiliar environment. The method includes blind user acquiring one or more images using a mobile device and invoking processing algorithms. Processing algorithms include one of Multi View Stereo and Structure from Motion, whereby algorithms construct a 3D representation of the environment being imaged. Further algorithms are applied to identify and assign attributes to objects in the imaged environment. The 3D representation is responsive to mobile device orientation. The environment is presented to the user via a touch screen, enabling the user to virtually explore the environment using touch, whereby objects being touched are identified, and associated with dimensional and other attributes.

10 Claims, 7 Drawing Sheets

(56) References Cited

U.S. PATENT DOCUMENTS

| | | | |
|---|---|---|---|
| 9,370,459 B2* | 6/2016 | Mahoney | G06K 9/00664 |
| 9,516,283 B2* | 12/2016 | Hilkes | H04N 7/185 |
| 9,539,164 B2 | 1/2017 | Sanders et al. | |
| 9,579,236 B2* | 2/2017 | Amedi | A61H 3/061 |
| 10,062,010 B2* | 8/2018 | Kutliroff | G06N 3/08 |
| 2013/0131985 A1 | 5/2013 | Weiland et al. | |
| 2013/0216093 A1* | 8/2013 | Lee | A61H 3/061 |
| | | | 382/103 |
| 2013/0250078 A1* | 9/2013 | Levy | A61F 9/08 |
| | | | 348/62 |
| 2013/0335543 A1* | 12/2013 | Hilkes | H04N 7/185 |
| | | | 348/62 |
| 2014/0085446 A1* | 3/2014 | Hicks | G09B 21/008 |
| | | | 348/62 |
| 2015/0323325 A1* | 11/2015 | Caporizzo | G01S 7/497 |
| | | | 701/400 |
| 2015/0339905 A1* | 11/2015 | Stevens | G08B 21/02 |
| | | | 340/4.1 |
| 2016/0055268 A1* | 2/2016 | Bell | G06F 17/5004 |
| | | | 703/1 |
| 2017/0299394 A1* | 10/2017 | Lee | G01C 21/206 |
| 2017/0318407 A1* | 11/2017 | Meister | H04S 7/303 |
| 2018/0061276 A1* | 3/2018 | Baca | H04N 13/207 |
| 2018/0143023 A1* | 5/2018 | Bjorke | G01C 21/206 |
| 2018/0177640 A1* | 6/2018 | Quesada Herv s | A61F 9/08 |
| 2018/0268220 A1* | 9/2018 | Lee | G06K 9/00691 |
| 2018/0293980 A1* | 10/2018 | Dwarakanath | A61F 9/08 |
| 2018/0315162 A1* | 11/2018 | Sturm | G06T 15/10 |
| 2018/0330184 A1* | 11/2018 | Mehr | G06F 17/18 |

OTHER PUBLICATIONS

S M. Seitz, et al, "A comparison and evaluation of multi-view stereo reconstruction algorithms," IEEE Conference on Computer Vision and Pattern Recognition, vol. 1, pp. 519-528, 2006.

Y. Furukawa and C Hernandez (2015), "Multi-View Stereo A Tutorial", Foundations and Trends® in Computer Graphics and Vision: vol. 9—No. 1-2, pp. 1-148.

Y-H. Lee, "Finding Object Depth Using Stereoscopic Photography," The 24th Workshop on Combinatorial Mathematics and Computation Theory, p. 450-459.

* cited by examiner

SYSTEMS AND METHODS FOR BLIND AND VISUALLY IMPAIRED PERSON ENVIRONMENT NAVIGATION ASSISTANCE

CROSS-REFERENCE TO RELATED APPLICATIONS

Not Applicable

FIELD OF THE INVENTION

The present disclosure relates generally to blind and visually impaired person aid systems and methods. More particularly, the present disclosure relates to a systems and methods for assisting blind and visually impaired people navigate new and unfamiliar environments.

BACKGROUND OF THE INVENTION

People with a limited or absent sense of sight require an alternate method for recognizing and navigating their physical environment. According to World Health Organization, 39 million people worldwide are legally blind and 246 million have low vision (www.who.int). Further, according to CDC, there are 3.4 million people in the United States who are either legally blind or substantially visually impaired (www.cdc.org). The rate of visual issues in the younger population has increased recently due to the blast-induced increase in Traumatic Brain Injury (TBI) associated with increased US military engagements, and TBI frequently produces visual impairments.

In the past, such people had to rely on other people, guide dogs, and canes for help in navigating environments. People helpers are rarely available, and guide dogs and canes provide only a limited amount of information to the blind person. Dogs can help guide a person around obstacles, or along a pre-trained route. Canes provide information on location of physical obstacles within immediate reach, but do not provide any information on the identity of such obstacles, or how to navigate around them. Blind people resort to guesses based on contextual interpretation of their assumed physical environment, i.e. I'm in a room and there is an object with a large flat surface and I feel empty space underneath—it could be a table.

Adaptive technologies based on various electronic approaches have been proposed and developed to provide solutions to the above identified problems. As a rule, they present information to the blind user through transforming environmental information into a usable sense, such as vibration, sound, or touch.

Some electronic devices use an emitted signal, such as an optical or an ultrasound pulse, and acquire a reflected signal. Examples are BuzzClip by Imerciv, which is worn like a button, or iGlasses by Maxiaids which are worn as glasses, and which use ultrasound to detect obstacles and alert wearer through vibration or audible tones (indiegogo.com/projects/the-buzzclip-wearable-mobility-tool-for-the-blind) (maxiaids.com/iglasses-ultrasonic-mobility-aid-clear-lens-maxiaids.com/iglasses-ultrasonic-mobility-aid-clear-lens). Similarly, optical ranging using laser sources is possible.

Another approach is to use GPS assistance to help blind people navigate predetermined routes. An example is Humanware's Trekker handheld GPS devices that provide verbal directions, information about nearby places of interest, public transportation information, etc.

Current technology is improving fast to assist disabled people, especially so with the proliferation of inexpensive and powerful smart phones. Specifically, assistive technology for blind people is evolving rapidly with the improvements in mobile devices such as smart phones and tablets and their embedded sensors. Smart assistants like Apple's VoiceOver provide an intuitive and convenient way for blind people to interact their mobile devices, access functions and interact with content. GPS and accelerometers provide information about mobile device relative position in space. High quality cameras provide high resolution images, both still and moving. Embedded processors allow sophisticated image processing algorithms to be run locally on the mobile device. High bandwidth network connections allow to offload functions that require more sophisticated and intensive processing to the cloud, and rapidly obtain processed results.

There are existing mobile device applications that provide assistive technology for blind people. LookTel by Ipplex recognizes and speaks the denomination of paper currency which is being captured by the camera. VizWiz by Rochci allows a user to send an image to sighted human volunteer along with a question, or to an automated engine for label identification. Color ID by GreenGar identifies colors of objects being captured by the camera. CamFind by CamFind and EyeSpy by My Eye Spy Pty identify some common objects in an image captured by the camera.

A common problem encountered by a blind person is understanding a new and unfamiliar environment, as for example when entering a room or space for the first time. A conventional approach for a blind person is to explore the walkable space with a cane, and use tactile feedback to identify objects. This is very time consuming, cumbersome, and potentially hazardous as the person can trip, bump into unexpected objects, touch dangerous surfaces such as a hot coffee maker or stove, etc. What is needed is a method for allowing a blind person to explore the space in a virtual environment, but with sufficient accuracy to be useful. Beneficially, such method would be based on an existing mobile device, such as iPhone, iPad, Android Phone and the like, that a user is likely to already own.

BRIEF SUMMARY OF THE INVENTION

In an exemplary embodiment, a method, performed by a mobile device includes acquiring an image of the environment, acquiring information about mobile device spatial orientation, and its relative distance to the objects in the environment, wherein mobile device comprises one or more of phone or tablet with an embedded camera, accelerometers, touch enabled screen and speakers. The method can further include providing image and sensor data acquisition in response to user request, processing data to present a plan of the image mapped to the device touch screen corresponding to the screen spatial orientation, being responsive to user touch of the screen, and providing verbal description of the objects in the image responsive to user touch.

The mobile device can be configured to take an image using a camera, wherein the mobile device can be configured to perform one of recognizing one or more objects in the image using image detection and processing algorithms to visually identify the objects. The location of the objects and environmental features such as open spaces and floors can be based on determining the orientation of the mobile device, camera focus distance to the objects, and on correlation of expected common object dimensions relative to the image.

The mobile device for blind and visually impaired person assistance includes a communication interface; a camera; a processor communicatively coupled to the communication interface and the camera; and memory storing computer-executed instructions that, when executed, cause the processor to: capture surrounding environment image, wherein the data is collected by the mobile device at user request. The memory storing computer-executed instructions that, when executed, can further cause the processor to receive, via the communication interface, information related to performing the equipment service at the site, and cause display of visual cues related to the equipment, in a field of view of the installer.

The memory storing computer-executed instructions that, when executed, can further cause the processor to: acquire and image through the camera and apply and automatic image detection and processing algorithms to visually identify objects and features in the image corresponding to the environment. The memory storing computer-executed instructions that, when executed, can further cause the processor to: acquire mobile device accelerometer reading to determine mobile device spatial orientation, and acquire camera focal distance information to determine distance to objects. The memory storing computer-executed instructions that, when executed, can further cause the processor to: re-compute image orientation to present blind user with a virtual representation mapped to mobile device screen, and to further provide verbal description of the objects and environmental features in response to user touch of particular areas of the screen corresponding to the object or feature location in the image.

It is an object of this invention to provide a method for allowing a blind or visually impaired person to explore a new or unfamiliar room or environment in a virtual environment, but with sufficient accuracy to be useful. Beneficially, such method would be based on an existing mobile device, such as iPhone, iPad, Android Phone and the like, that a user is likely to already own.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE INVENTION

In various exemplary embodiments, systems, and methods for assisting blind and visually impaired people are described. The systems and methods may use mobile devices (e.g. iPhone, iPad, Android phone, etc.) with an embedded capability for taking digital photographs, determining mobile device special orientation, remapping digital images based on changed device orientation, processing images to identify objects and environmental features, and providing audio feedback responsive to user touch to specific areas of the image. This approach is advantageous for assisting blind and visually impaired people identify the objects and features of a new and unfamiliar environment, such as upon entry into a new room. Further, the systems and methods enable identification of potentially hazardous or dangerous situations or objects, such operating kitchen appliances, fireplaces, lit lamps and the like.

Figure 1:
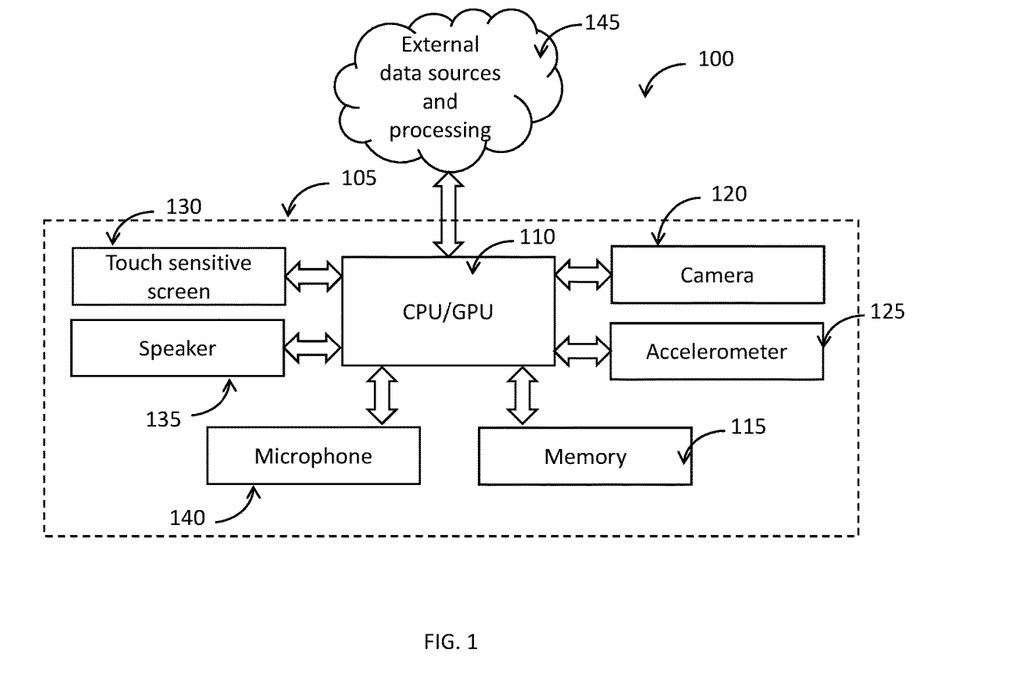
FIG. 1 is a system for assisting blind and visually impaired people navigate a room or a new and unfamiliar environment.

Referring to FIG. 1, in an exemplary embodiment, a diagram illustrates a system 100. The system 100 includes a mobile device 105, which may further be comprised of processing unit 110 which is communicatively coupled to memory 115, digital camera 120, positional sensors 125, touch sensitive screen 130, speaker 135, and microphone 140. The system 100 may include mobile device 105 communicating with an external data sources and processing units 145. The external data source and processing unit 145 can be a Central Office (CO), Point-of-Presence (POP), Data Center, etc.

The mobile device 105 has access to both computing power and information via wireless connectivity to the external source 145 as well as locally, without network connectivity. Compute processing and information can come from the mobile device 105 itself. Accordingly, the mobile device 105 can be utilized to assist blind or visually impaired person.

Figure 2:
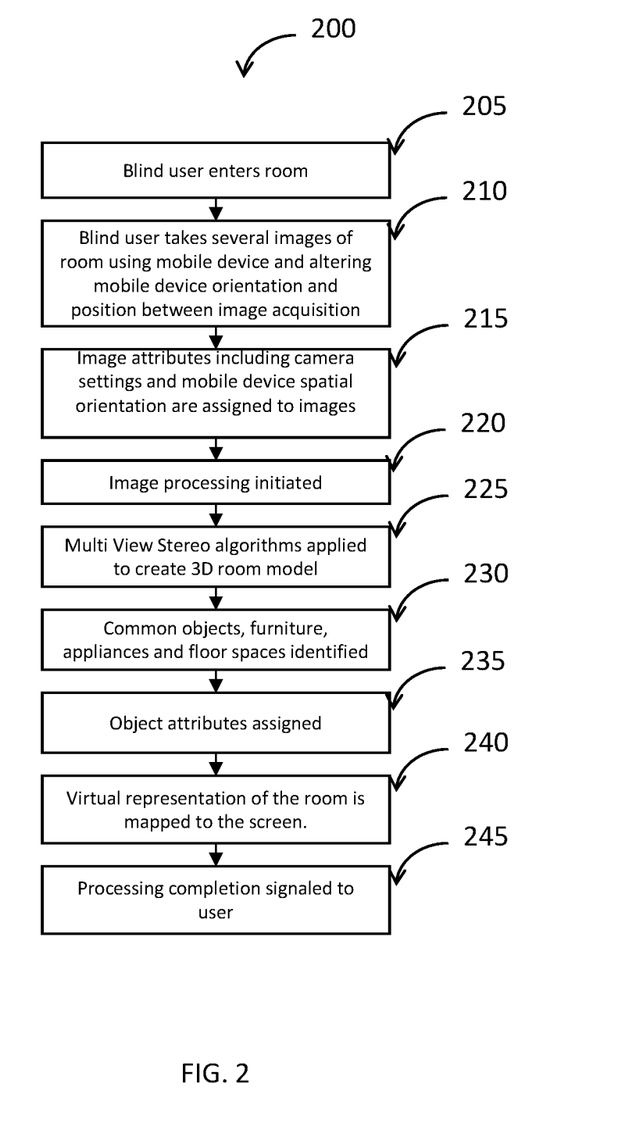
FIG. 2 is a flowchart of a method for acquiring and processing a set of images of a room and unfamiliar environment.

According to the method 200 of FIG. 2 for use of the exemplary embodiment, a blind or visually disabled user enters a room or a new or unfamiliar space in step 205. In step 210, the user, using mobile device 105 and digital camera 120, acquires one or more images of the room, which are then stored in memory 115. A single image does not contain sufficient information to provide a representation in real 3D space, which is required for an accurate spatial mapping. Therefore, a user may do one of using a mobile device with multiple cameras (e.g mobile phones with dual cameras such as iPhone 7, LG V20, etc.), and taking one or more pictures with a relative spatial displacement of the mobile device 105, and relying on object location and identification algorithms and obtaining dimensional information by assuming typical expected dimensions for well-known everyday objects (e.g. chairs, couches, doors, windows, etc.).

In step 215, the mobile device 105 interrogates its positional sensors 120 and establishes relative displacement and rotation of the mobile device for every acquired image.

Upon completion of the image acquisition, in step 220 user initiates image processing, In step 225, a processing unit 105 applies a set of predetermined computations to establish relative position of the image points in 3D real space. First, the optical parameters of the camera lens such as focal distance and numeric aperture are obtained. Well known algorithms are applied to correct for image distortion, as for example would be obtained with a wide-angle lens.

The algorithms for mapping image points to corresponding 3D real space coordinates are then applied, based on the 5 dimensional information obtained either from multiple images, or from well-known everyday object size estimates. These algorithms are well known in the art, as for example described in J. Mrovlje, et al, "Distance measuring based on stereoscopic pictures," $9^{th}$ International PhD Workshop on Systems and Control, October 2008, and Y-H. Lee, et al, "Finding object depth using stereoscopic photography," The $24^{th}$ Workshop on Combinatorial Mathematics and Computational Theory, pp. 450-459 for obtaining distance information to the object.

More comprehensive algorithms may be used instead, which are commonly known as Multi View Stereo algorithms, and have been extensively studied, with a goal of reconstructing 3D view from multiple known camera viewpoints. A detailed description of several such algorithms is provided in S. M. Seitz, et al, "A comparison and evaluation of multi-view stereo reconstruction algorithms," IEEE Conference on Computer Vision and Pattern Recognition, volume 1, pages 519-528, 2006. A more recent detailed description is provided by Yasutaka Furukawa and Carlos Hernández (2015), "Multi-View Stereo: A Tutorial", Foundations and Trends® in Computer Graphics and Vision: Vol. 9: No. 1-2, pp 1-148 (dx.doi.org/10.1561/0600000052).

Following the definitions of Seitz, et al, the system 100 can apply the algorithms that fall into any of the four classes of Multi View stereo techniques. The first algorithm type uses surface generation by defining a cost function directly on a 3D volume. A second algorithm type iteratively finds an optimal surface by minimizing a cost function, as for example done with a space carving technique. A third algorithm type computes a depth map for each view, and these depth maps are merged at a post process stage. The fourth algorithm type extracts and matches a subset of feature points for each image and then fits a surface to the reconstructed image.

Substantial algorithm simplification and speed up is possible since mobile devices are capable of providing spatial position and orientation information. This information can be used to provide accurate initial estimates for Multi View Stereo algorithms, thereby allowing processing to fit within the capability of mobile devices, and be completed in reasonable time to be useful to the blind person.

In step 230, objects are automatically recognized and identified within the space, using any number of existing algorithms and approaches. One approach is to use an open source computer vision library OpenCV (www.opencv.org), with an algorithm such as Maximally Stable Extremal Regions (MSER). More sophisticated feature extraction approaches such as Haar-like features, Histogram of Oriented Gradients (HOG), Scale-Invariant Feature Transform (SIFT), Speeded Up Robust Feature (SURF) etc. can be used.

In step 235, important attributes can be associated with objects. The main attribute associated with objects would be object dimensions, including overall room or space dimension. Other attributes are also envisaged such as low objects within floor spaces that can represent a tripping hazard, open and closed doors, potentially dangerous objects such as fireplaces, kitchen appliances, and the like.

It is advantageous for the method 200 to be sufficiently fast that a result is available within a reasonable time, such as within 1 min or less. Therefore, amount of processing and available information will depend on the available system 100 processing power. Preferentially, more information may be processed and provided on more powerful systems, and less information on less powerful ones.

In step 240, a virtual representation of the room or new environment or space is mapped to the screen 130. And process completion is signaled to the user in step 245 using speaker 135 or haptic vibration feedback.

Figure 3:
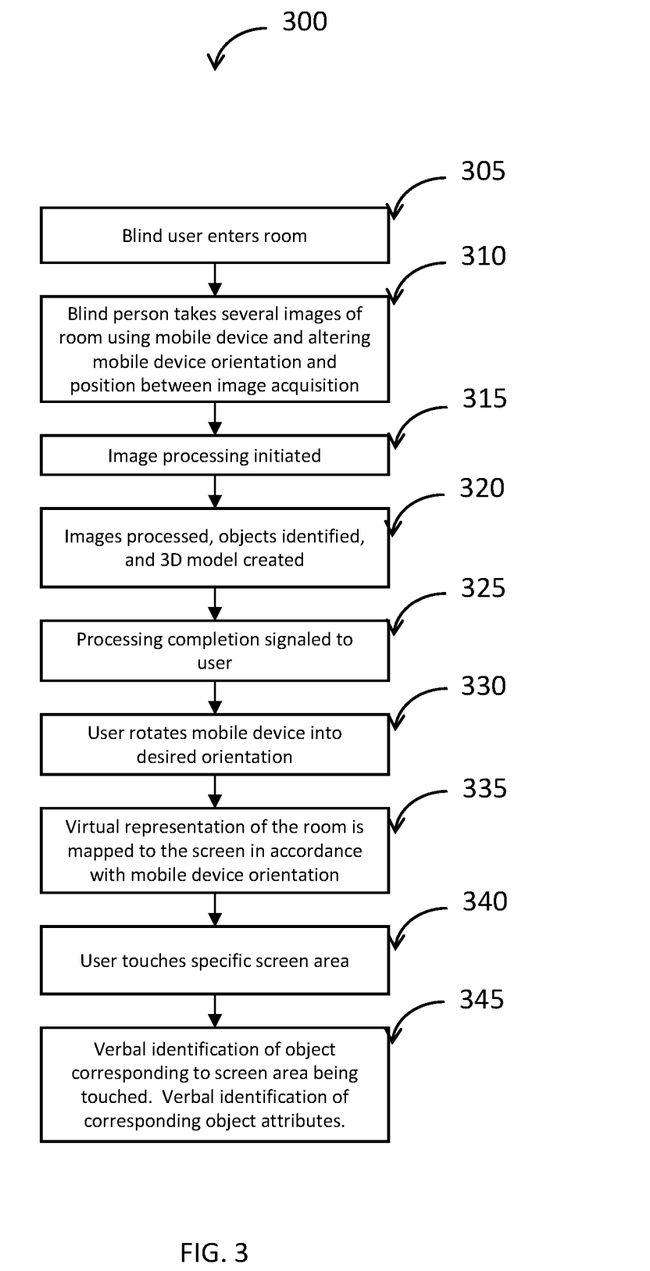
FIG. 3 is a flowchart of a method for using the mobile device and processed image information to assist a blind or visually impaired user virtually navigate a room and unfamiliar environment.

Referring to FIG. 3, in an exemplary embodiment, a flowchart illustrates a method 300. The method 300 contemplates operation of the system 100 for blind or visually impaired user assistance. According to method 300, a user enters a room or an unfamiliar environment in step 305. Preferentially, the user would stop right at the door without proceeding into the room or unfamiliar environment.

In step 310, using device 105, user acquires several images of the space, each image being acquired using different position of the device and orientation of the device relative to the just entered room. When completed, in step 315 the user initiates processing by one of a gesture and verbal command. In step 320, the system 100 performs computations following steps 225, 230, and 235 of FIG. 2. In step 325, completion of the processing step is indicated via a predefined audio tone via speaker 135 or vibration pattern.

In step 330, user rotates mobile device 105 into desired orientation. For example, screen 130 can be aligned substantially coplanar with the floor. In this case, in step 335, 3D model representation is mapped to screen 130 as a top-down view of the imaged room or space, with corresponding objects outlined in correct relative positions.

System 100 displays a projection of the room or new environment on touch sensitive screen 130. It should be understood that the blind or visually impaired user may not be able to see the image on the screen, and there may be no visible image on the screen. However, the image is mapped to the screen 100 such that a user touch in a specific area of the screen (step 340) provides a verbal indication of the object being touched and its associated attributes (step 345).

Following method 300, a blind or visually impaired user can virtually explore the room or new and unfamiliar space, avoiding potential hazards and improving speed and comfort.

Figure 4:
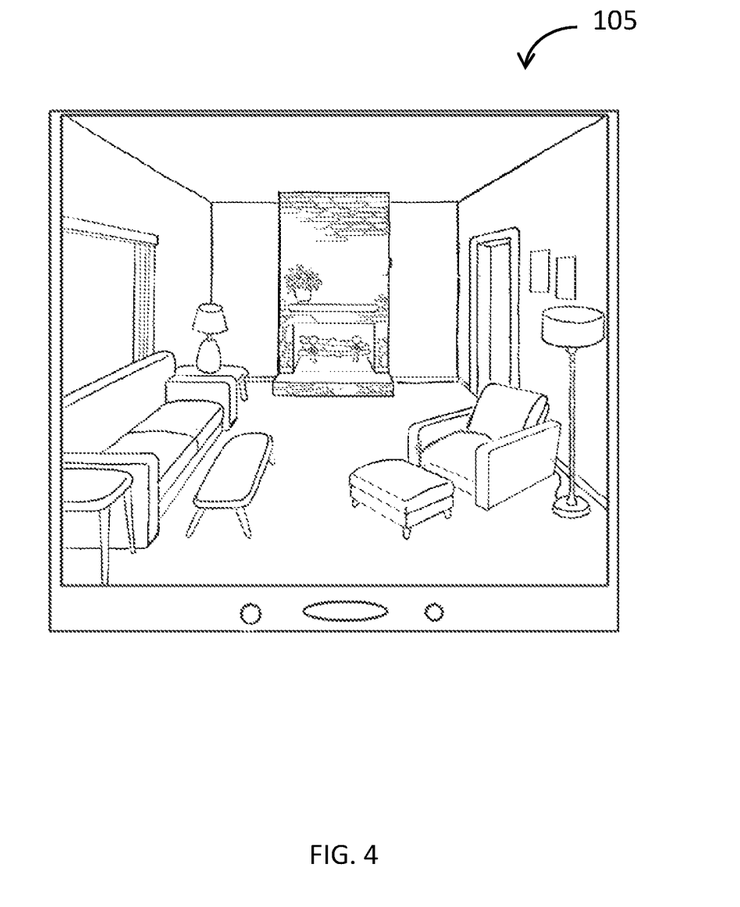
FIG. 4 is a mobile device with an exemplary image of a room taken by the blind or visually impaired person upon entering a room.

Referring to FIG. 4, in an exemplary embodiment, a mobile device 105 is shown with an exemplary image being displayed on screen 130. The image represents a room on screen 130 when the device 105 is oriented with its camera 120 substantially facing the room, such as when a user would be acquiring images in step 310 of FIG. 3. As the user tilts the device 105, the image rotates in a manner corresponding to the device orientation.

Figure 5:
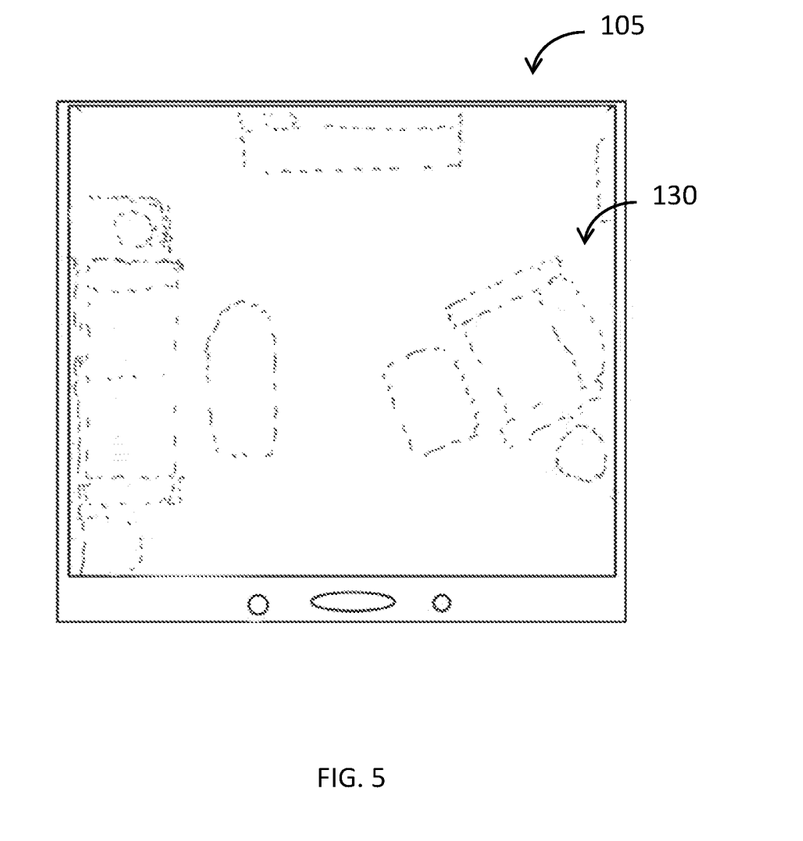
FIG. 5 is a mobile device with an image of a room transposed into a horizontal projection when mobile device screen is coplanar with the floor.

Referring to FIG. 5, in an exemplary embodiment, when screen 130 is substantially horizontal and aligned coplanar with the floor of the room, the displayed image represents a top-down view of the room. In effect, a map of the room is created on the screen, allowing the user to use touch screen to explore the space in a virtual manner.

Figure 6:
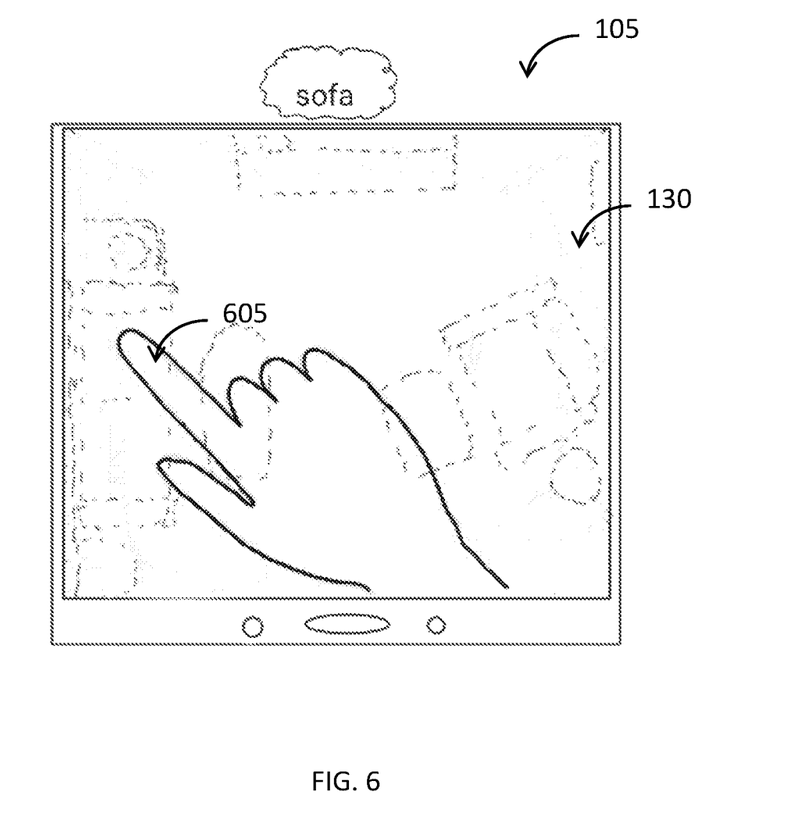
FIG. 6 is a mobile device with an image of a room transposed into a horizontal projection when mobile device screen is coplanar with the floor, illustrating a user touching area corresponding to the sofa.

Referring to FIG. 6, in an exemplary embodiment, the user 605 touches an area on screen 130 corresponding to an object identified in processing step 230 as "sofa", the speaker 135 informs the user that a "sofa" is being touched.

Figure 7:
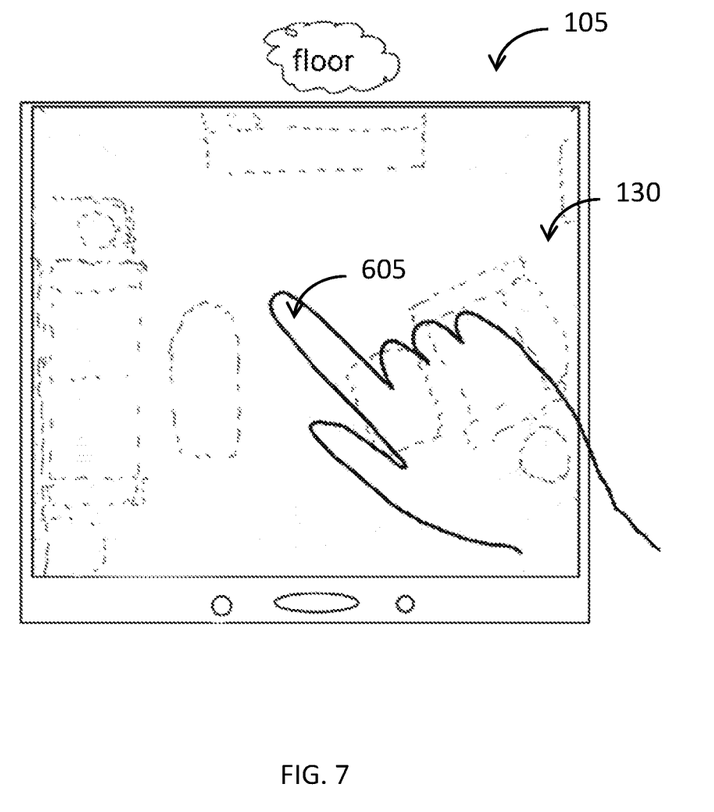
FIG. 7 is a mobile device with an image of a room transposed into a horizontal projection when mobile device screen is coplanar with the floor, illustrating a user touching area corresponding to the floor.

Referring to FIG. 7, in an exemplary embodiment, the user 605 touches an area on screen 130 corresponding to an object identified in processing step 230 as "floor", the speaker 135 informs the user that a "floor" is being touched. Using touch, the user is therefore able to substantially explore the room without physically moving through it, understanding the objects located in the room, their relative positions dimensions and orientation, potential paths through the room, location of other doors, and the like. The user is also presented with object attributes identified in step 235, such as potential tripping hazards, open/closed status of doors, potential appliance hazards, and the like.

The projection of the room or new environment changes as the mobile device 105 and screen 130 are rotated by the user. If the user makes the screen horizontal, the view essentially displays a top-down view of the room, like a map. Screen edges become an outline of a room and moving user finger around the screen is like walking around the room and feeling objects.

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A method, performed by a mobile device, for assisting a visually impaired user, the method comprising:
   receiving, from the mobile device associated with the visually impaired user, one or more images relating to a room or new environment, wherein the one or more images are acquired by the mobile device upon the visually impaired user entering the room or new environment, wherein the mobile device comprises a camera, processor, memory, touch-enabled screen, audio output, and vibration output;
   processing the one or more images to obtain a three-dimensional model representation of the room or new environments and identifying one or more object attributes of one or more identified objects within the room or new environment;
   processing the three-dimensional model to obtain a two-dimensional projection of the room or new environment including the one or more identified objects and the one or more identified object attributes,
   mapping the two-dimensional projection to the touch-enabled screen of the mobile device such that edges of the touch-enabled screen form an outline of the room or new environment;
   playing back audio related to the one or more identified objects responsive to the visually impaired user touching the two-dimensional projection on the touch-enabled screen, wherein the audio includes a distance to the object being touched and/or the object attributes of the object being touched.

2. The method of claim 1, further comprising applying an image transformation function to correct the one or more images for optical aberrations.

3. The method of claim 1, wherein the processing of the one or more images is comprised of applying one of multi-view stereo and structure from motion algorithms.

4. The method of claim 1, wherein the processing of the one or more images includes a step of associating spatial dimensions with the one or more objects in the one or more images.

5. The method of claim 1, wherein the one or more identified object attributes comprise one or more of material, color, hazard condition, and warning.

6. The method of claim 1, wherein the mobile device is configured to obtain its spatial orientation during image acquisition.

7. The method of claim 1, wherein the two-dimensional projection mapped to the touch-enabled screen is responsive to an orientation of the mobile device.

8. The method of claim 1, wherein the mobile device communicates to an external processing unit.

9. A mobile device for assisting a visually impaired user when entering a room or new environment, the mobile device comprising:
   a communication interface;
   a camera;
   a touch-enabled screen;
   a speaker;
   a microphone;
   a processor communicatively coupled to the communication interface and the camera; and
   memory storing computer-executed instructions that, when executed, cause the processor to:
      capture one or more images, wherein the one or more images are acquired by the camera initiated by the visually impaired user;
      process the one or more images to obtain a three-dimensional model of the room or new environment and identifying one or more object attributes of one or more identified objects within the room or new environment;
      process the three-dimensional model to obtain a two-dimensional projection of the room or new environment including the one or more identified objects and the one or more identified object attributes;
      map the two-dimensional projection on the touch-enabled screen of the mobile device such that edges of the touch-enabled screen form an outline of the room or new environment;

play back audio related to the one or more identified objects responsive to the visually impaired user touching the two-dimensional projection on the touch-enabled screen, wherein the audio includes a distance to the object being touched and/or the object attributes of the object being touched.

10. The mobile device of claim 9, wherein the memory stores computer-executed instructions that, when executed, further cause the processor to:

run automatic detection and processing algorithms on the one or more images to identify the one or more object attributes of the one or more identified objects.

* * * * *